United States Patent [19]

Sturm

[11] 4,435,599

[45] Mar. 6, 1984

[54] PARA-NITRODIPHENYLAMINE SYNTHESIS

[75] Inventor: Budd H. Sturm, Hartville, Ohio

[73] Assignee: The Goodyear Tire & Rubber Company, Akron, Ohio

[21] Appl. No.: 444,633

[22] Filed: Nov. 26, 1982

[51] Int. Cl.³ .................... C07C 85/18; C07C 85/24
[52] U.S. Cl. ................................................. 564/433
[58] Field of Search ....................................... 564/433

[56] References Cited

U.S. PATENT DOCUMENTS 2,156,792 5/1938 Neal et al. ............... 564/433 X
4,046,810 9/1977 Moggi et al. ................. 564/433
4,057,581 11/1977 Krall et al. .................. 564/433
4,238,407 12/1980 Fauss et al. ............... 564/433 X

FOREIGN PATENT DOCUMENTS 101496 4/1979 Poland ......................... 564/433

*Primary Examiner*—Paul F. Shaver
*Attorney, Agent, or Firm*—D. O. Nickey

[57] ABSTRACT

There is disclosed a process for the synthesis of para-nitrodiphenylamines wherein the improvement is characterized in that a specific co-catalyst system is utilized. More specifically, a zinc (II) compound (zinc in the plus two oxidation or valence state), is used in conjunction with copper or a copper compound as a co-catalyst system in the preparation of para-nitrodiphenylamines.

15 Claims, No Drawings

PARA-NITRODIPHENYLAMINE SYNTHESIS

TECHNICAL FIELD

The present invention is concerned with a co-catalyst system used to prepare para-nitrodiphenylamines wherein the co-catalyst system overcomes numerous disadvantages presently found in the production of para-nitrodiphenylamines.

BACKGROUND ART

This invention relates to an improvement in the synthesis of para-nitrodiphenylamines. Para-nitrodiphenylamines are useful intermediates in the formation of rubber antioxidants and antiozonants. Their generic formula is as follows:

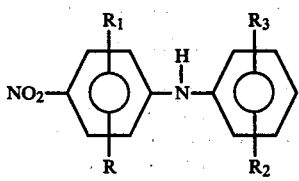

wherein R and $R_1$ are selected from the group consisting of hydrogen radicals and alkyl radicals of 1 to 9 carbon atoms; $R_2$ and $R_3$ are selected from the group consisting of hydrogen radicals, alkyl radicals from 1 to 9 carbon atoms, alkoxy radicals of 1 to 6 carbon atoms and cycloalkyl radicals of 5 to 6 carbon atoms.

Presently, these compounds are synthesized by reacting (1) para-halonitrobenzenes conforming to the following structural formula:

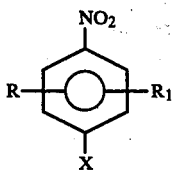

wherein X is a halogen selected from the group consisting of chlorine and bromine; and wherein R and $R_1$ are defined above; (2) with a primary aromatic amine of the following structural formula:

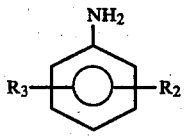

wherein $R_2$ and $R_3$ are defined as above; (3) in the presence of a neutralizing agent, selected from the group consisting of alkali metal salts, oxides of alkali metal salts and alkali metal hydroxides; (4) in the presence of a catalyst in a concentration of at least 0.1 parts by weight per hundred parts per weight of the para-halonitrobenzene; (5) at a temperature of 170°–250° C.; (6) at a pressure of from atmospheric to about 300 kPa (kilopascals) and (7) with an excess of primary aromatic amine of from 3 to 300 percent.

Presently commercially accepted processes for the production of para-nitrodiphenylamines are described in British Pat. Nos. 798,148; 834,510; German Pat. No. 185,663; and U.S. Pat. No. 3,155,727.

Polish Pat. No. 101,496 (a copy of which is attached and the translation thereof) discloses a method for producing para-nitrodiphenylamines from aniline and para-chloronitrobenzene in the presence of an acid acceptor with concomitant azeotropic water removal using cupric-oxide and dimethylformamide or copper-metal as the catalyst, the improvement being the addition of zinc dust in an amount no larger than 2 percent relative to para-chloronitrobenzene. This Polish patent does not suggest or disclose the use of zinc (II) compounds, (zinc in the plus two oxidation or valence state) to achieve a substantial reduction in the reaction times and provide for increased yield with fewer side reactions.

In present commercial applications a copper or copper compound catalyst gives moderately good yields of para-nitrodiphenylamines (75–90 percent), but the reaction times are somewhat long (10 to 24 hours) and product purity is less than desirable. These presently accepted means of synthesis are usually conducted at temperatures lower than 205° C. and at times in excess of 12 hours. Further, the presently accepted commercial synthesis route suffers from poor product quality in that a fair amount of tars and by-products are present in the final product. The improvement of the present application is characterized in that a copper or copper compound plus a zinc (II) compound is used as a co-catalyst system for the preparation of para-nitrodiphenylamines.

A presently accepted catalyst is copper cyanide, however, as a catalyst it has major drawbacks in that the aqueous effluent from the reaction contains amounts of copper plus cyanide ions. Present environmental concerns dictate that such effluents are not acceptable in the environment.

U.S. Pat. No. 4,155,936 by the present applicant is herein incorporated by reference and made a part hereof. Specifically, U.S. Pat. No. 4,155,936 is concerned with the incorporation of solubilizing agents in the reactiom mixture to reduce reaction times and improve yields.

U.S. Pat. No. 4,155,936 and other publications do not suggest or disclose the use of a co-catalyst system with zinc (II) compounds in the preparation of para-nitrodiphenylamines from para-halonitrobenzenes and primary aromatic amines.

The present invention provides a solution to the problems of long reaction times, limited number of suitable catalysts and environmentally unsound effluents from the reaction. In addition, the present invention allows for the use of relatively insoluble, low surface area copper and copper compounds in conjunction with zinc (II) compounds which would otherwise be unacceptable on a commercial basis.

The patents and literature cited do not suggest or disclose that unexpected improvements in the synthesis of para-nitrodiphenylamines can be obtained. More specifically, the process of the present invention provides a means for avoiding cyanide ions in the waste water effluent, improved efficiency of the reaction and improved product yield and quality.

DISCLOSURE OF THE INVENTION

There is disclosed a process wherein (1) a para-halonitrobenzene conforming to the following structural formula:

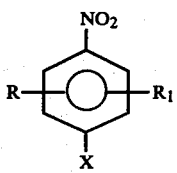

wherein R and $R_1$ are selected from the group consisting of hydrogen radicals and alkyl radicals of 1 to 9 carbon atoms and wherein X is a halogen selected from the group consisting of chlorine and bromine; is reacted with (2) a primary aromatic amine of the following general structural formula:

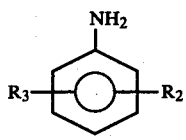

wherein R and $R_3$ are selected from the group consisting of hydrogen radicals, alkyl radicals of 1 to 9 carbon atoms and alkoxy radicals of 1 to 9 carbon atoms and cycloalkyl radicals of 5 to 6 carbon atoms; in the presence of (3) a neutralizing agent, selected from the group consisting of alkali metal salts, oxides of alkali metal salts and alkali metal hydroxides; (4) a copper catalyst at a concentration of at least 0.05 parts by weight per hundred parts by weight of the para-halonitrobenzne; (5) at a temperature of 170°–250° C.; (6) at a presence from atmospheric to about 300 kPa; (7) with an excess of primary aromatic amine; wherein the improvement is characterized in that the copper catalyst has added thereto a zinc (II) compound selected from the group comprising (a) zinc (II) salts, (b) zinc (II) oxides, (c) zinc (II) sulfides and (d) organometallic zinc (II) compounds.

There is also disclosed a process for producing p-nitrodiphenylamine from aniline and p-chloronitrobenzene wherein the reaction is conducted (a) at a temperature from 100° to 250° C., (b) in the presence of an alkaline metal salt, (c) with an excess of aniline, (d) at super atmospheric pressure, (e) in the presence of a solubilizing agent, (f) with at least 0.1 parts by weight per 100 parts by weight of the p-chloronitrobenzene of a catalyst, the improvement characterized in that the catalyst is a mixture of (A) at least one copper compound selected from a group comprising cupric oxide, cupric nitrate, cuprous cyanide, copper acetyl acetate, cupric chloride, cuprous chloride and powdered copper; and (B) at least one zinc (II) compound selected from a group comprising zinc acetate, zinc sulfide, zinc stearate, zinc oxide, zinc chloride, zinc carbonate and zinc dimethyldithiocarbamate.

Representative of the zinc (II) compounds that can be used in the process of the present invention are: zinc acetate, zinc oxide, zinc chloride, zinc sulfide, zinc stearate, zinc carbonate, and zinc dimethyldithiocarbamate.

Representative of the copper compounds that can be used in the process of the present invention are: CuO, $Cu_2O$, copper dust, $Cu_2(CN)_2$, brass powder, copper acetyl acetate, $CuCl_2$, $CuSO_4$, $CuSO_4$ $5H_2O$, $Cu_2Cl_2$, $CuCl_2$, $CuBr_2$ and cupric nitrate.

The process of the present invention can be used with or without solubilizing agents as disclosed in U.S. Pat. No. 4,155,936. The work-up of the final product is described in U.S. Pat. No. 4,155,936.

BEST MODE FOR CARRYING OUT THE INVENTION

The following examples are intended to illustrate and not to limit the scope of the present invention. All the following experiments were carried out in a one liter three-necked flask equipped with a stirrer, dropping funnel, thermometer, and a Claisen adapter with a vertical air condenser connected to a jacketed distillation head. The distillation head lead to a water condenser with a Dean-Stark trap and finally into a 100 milliliter Erlenmeyer receiving flask. A small pump with polypropylene tubing was used to recycle the toluene-aniline solutions back to the dropping funnel.

EXPERIMENT 1

100 grams of para-nitrochlorobenzene (PCNB), 50 grams of anhydrous $K_2CO_3$ and 150 grams of aniline were charged to the one liter three-necked flask. A solubilizing agent, i.e. Carbowax TM Methoxy PEG-2000 and the catalyst system were added with stirring. The mixture was then heated to 185° C., using an electric heating mantle. 50 ml of toluene was added at a rate of 1 to 2 drops per second and the pot temperature was maintained at 185°–190° C. Overhead temperatures were maintained at approximately 108°–128° C. The water of reaction was collected in the Dean-Stark trap and measured during the course of the reaction. The toluene-aniline solution was pumped to the dropping funnel and added back to the reaction. The catalyst used was powdered CuO and ZnO consisting of 66.8 weight percent CuO and 33.6 weight percent ZnO (independent analysis for copper and then zinc results in the 100.4 percent total). One gram of the catalyst system was added to the reaction mixture along with two grams of the solubilizing agent.

From the amount of water collected it was determined that after five hours the above reaction was finished for all practical purposes.

The reaction mixture was cooled to 125°–130° C., then 200 ml of toluene was added. The reaction temperature dropped to just below 100° C. 180 milliliters of distilled water was added with rapid stirring and the temperature was maintained at 86°–88° C. for one-half hour. The stirrer was turned off, the water layer was decanted, cooled to room temperature, filtered, and sent out for analysis. The reaction solution was then azeotroped dry, filtered and stripped at 185° C. using an aspirator. A 88.3% yield of para-nitrodiphenylamine was realized. Analysis of the waste water indicated that there were no $CN^-$ ions and a decrease in the $Cu^+$ ions in relation to the presently accepted means of synthesis wherein $Cu_2(CN)_2$ is used as the catalyst system.

EXPERIMENTS 2–12

The procedure described in Experiment 1 was followed except that the type and amount of the catalyst system was varied, the type and amount of the solubilizing agent was varied and the reaction time varied as indicated.

Table I contains the % true yield of product, the COD (chemical oxygen demand) of the water effluent and a water analysis for Experiments 1–12.

TABLE I

Experiments 1-12, Analysis of Product & Waste Water

| Exp. | Catalyst (gms) | Solubilizing Agent (gms) | Hours Reaction Time | % True Yield p-NO$_2$DPA[c][d] | mg COD/Liter[e] | Cu$^+$ ppm[f] | Zn$^{++}$ ppm[f] | CN$^-$ ppm[g] |
|---|---|---|---|---|---|---|---|---|
| 1 | 1 gm CAT A[h] | 2 gms I. CA-897[b] | 5 | 88.3 | 15,600 | 1.9 | 12.5 | — |
| 2 | 1 gm Cu$_2$(CN)$_2$ | None | 14 | 80.5 | 24,000 | 569 | — | 212 |
| 3 | 1 gm Cu$_2$(CN)$_2$ | 2 gms M-2000[a] | 5 | 86.2 | 14,200 | 227 | — | 187 |
| 4 | 1 gm Cat A | None | 11.5 | 87.6 | 17,100 | 0.9 | 3.5 | — |
| 5 | 1 gm Cat A | 4 gms M-2000 | 3 | 90.2 | 17,300 | 0.6 | 1.8 | — |
| 6 | 1 gm Cat B[i] | 4 gms M-2000 | 4 | 85.2 | 17,000 | 1.3 | 4.0 | — |
| 7 | 1 gm Cat A | 2 gms M-2000 | 5 | 88.2 | 18,400 | 0.7 | 3.3 | — |
| 8 | 1 gm Cat A | 1 gm M-2000 | 6.5 | 88.1 | 15,400 | 3.5 | 18.4 | — |
| 9 | 0.5 gms Cat A | 2 gms I. CA-897 | 7 | 85.3 | 15,500 | 0.6 | 2.8 | — |
| 10 | 0.25 gm Cat A | 2 gms I. CA-897 | 10 | 78.3 | 16,500 | 0.9 | 1.5 | — |
| 11 | 0.125 gms Cat A | 2 gms I. CA-897 | 13.5 | 52.2 | 17,000 | 1.9 | 7.2 | — |
| 12 | 2 gms Cat A | 4 gms M-2000 + Na$_2$CO$_3$ (40 gms) | 14 | 68.0 | 8,800 | 0.6 | 1.0 | — |

[a]M-2000 is Union Carbide's Carbowax Methoxy PEG-2000.
[b]I. CA-897 is GAF's IGEPAL CA-897.
[c]% true yield p-NO$_2$DPA = % crude yield times % p-NO$_2$DPA/100.
[d]p-NO$_2$DPA is para-nitrodiphenylamine. Determined L C Bonded Nitrile Column, Method AR-396.
[e]C.O.D. Analysis is Chemical Oxygen Demand determined by Oceanography Ampule Method.
[f]Metals Analysis Atomic Absorption Spectrophometric Method (AAS).
[g]CN$^-$ Method AR 172.
[h]Cat A = 66.8 wt % CuO and 33.6 wt % ZnO with a area of 59 sq. meters/gm.
[i]Cat B = 59.4% by wt CuO and 41.2% ZnO with a surface area of 46 sq. meters/gm.

From the data contained within Table I, it is evident that Catalyst A (66.8% CuO and 33.6% ZnO) with no solubilizing agent (Experiment 4) gave a better reaction than did Cu$_2$(CN)$_2$ (Experiment 2). Also, a better quality product (87.6% p-NO$_2$DPA vs. 80.5%), a dramatic reduction of Cu$^+$ in the waste water (0.9 ppm vs 569, almost a 1000X reduction) and complete elimination of CN$^-$ was obtained. COD analysis of the waste water was also better (17,100 vs 24,000).

Catalyst A with a 2% level of Carbowax Methoxy PEG-2000 (Experiment 3, based on weight of PCNB) gave a slightly better quality product and reaction than did Cu$_2$(CN)$_2$ (88.2% p-NO$_2$DPA vs 86.2%, 0.7 ppm Cu$^+$ vs 227 ppm, 18,400 mg COD/Liter vs 14,200, Experiment 7 vs Experiment 13).

Catalyst A with a 4% level of Carbowax Methoxy PEG-200 (by wt of PCNB) gave a better reaction and product than the catalyst B (Experiment 5 vs Experiment 6).

Catalyst A, with a 2% level of IGEPAL CA-897 (based on the weight of PCNB), gave an equivalent reaction and product when compared to the Carbowax run (5 hrs reaction time, 88.3% p-NO$_2$DPA vs 88.2%) and a somewhat equal waste water analysis when comparing Experiment 1 vs Experiment 7.

Attempts to cut the level of Catalyst A when used with a 2% level of IGEPAL CA-897 solubilizing agent (based on the weight of PCNB) had only limited success (comparing Experiment 1 vs Experiment 9 vs Experiment 20 vs Experiment 11). From the data in Table I, a 0.5% level of Catalyst A (based on the weight of PCNB) would be the absolute minimum.

Filtration of the azeotroped dried organic reaction solution presented no problems in the laboratory because of small batches. Most of the unreacted and undissolved catalyst came out in the water layer. Some undissolved catalyst was carried over in the organic layer. After the azeotrope drying operation, some problems could be encountered in the filtration step at a commercial facility because of the very fine undissolved particles in the organic solution and size of batch. A very complete water-organic solution separation in the commercial facility would minimize this problem.

Reactions in glassware are normally run with a 50% higher level of aniline than in commercial plant. Lowering the level of aniline in glassware reactions to plant levels results in a large drop of p-NO$_2$DPA content. Past experience of going from the higher glassware aniline reactions to the lower levels in the plant have presented no problems. The two systems in the past have had a good correlation in changes of catalyst and solubilizing agents, despite the differences in levels of aniline.

The advantages of the present invention over the presently accepted Cu$_2$(CN)$_2$ route include:
(1) reduction of pollutants in the effluent, with elimination of CN$^-$ and in a dramatic reduction of Cu$^+$;
(2) faster reaction;
(3) improved yield of p-NO$_2$DPA and a corresponding reduction of impurities;
(4) possible reuse of the catalyst system;
(5) lower production costs due to lower energy requirements and more efficient production.

EXPERIMENT 13

Seven catalysts were screened in the process of the present invention in Experiments 13-19. The catalyst systems are listed and described in Table II. The equipment and the procedure were as described in Example I.

TABLE II

Experiments 13-19

| Exp. | % Catalyst wt % on wt PCNB | Hrs. Run | % True Yield p-NO$_2$DPA |
|---|---|---|---|
| 13 | 1% CuO 59 m$^2$/gm | 15½ | 77.5 |
| 14 | Above Cat. 0.33% Zn | 12 | 83.4 |
| 15 | 1% CuO + 0.33% ZnS | 10.5 | 88.1 |
| 16 | 1% CuO + 0.33% Zn Stearate | 7 | 87.9 |
| 17 | 1% CuO + 0.33% Zn(Ac)$_2$.2H$_2$O | 8.75 | 84.4 |
| 18 | 1% Cu$_2$(CN)$_2$ | 14 | 80.5 |
| 19 | 1% Cu$_2$(CN)$_2$ + 0.33% Zn(Ac)$_2$.2H$_2$O | 6.5 | 92.9 |

From Table II it can be concluded that Zn (II) compounds speed up the reaction and increase the yield of para-nitrodiphenylamine when compared to other co-catalysts; see Experiment 13 vs 14, 15, 16 and 17, also see Experiments 18 vs 19.

It must be remembered that none of the runs listed above contain a polyether which is a surfactant. The use of polyethers or surfactants in the reaction of the present invention tends to increase the yield of product. It appears as if the effects of the surfactant are additive to the Zn (II) effects on the reaction, Table III demonstrates this effect.

Other experiments following the procedure set out in Ex. 1 were performed to determine the optimum level of Zn(II) in the catalyst system and the surfactant. Table IV sets out the results.

TABLE IV

Experiments 24–26

| Exp. | Catalyst | Surfactant* | Hrs Rxn. | % True Yield p-NO$_2$DPA | COD MgO$_2$/L | Cu$^+$ ppm | Cn$^-$ ppp |
|---|---|---|---|---|---|---|---|
| 2 | 1% Cu$_2$(CN)$_2$ | — | 14 | 80.5 | 24,000 | 569 | 212 |
| 3 | 1% Cu$_2$(CN)$_2$ | 2% M-2000 | 5 | 86.2 | 14,200 | 227 | 187 |
| 4 | 1% L-593 | — | 11.5 | 87.6 | 17,100 | 0.9 | — |
| 7 | 1% L-593 | 2% M-2000 | 5 | 88.2 | 18,400 | 0.7 | — |
| 13 | 1% CuO(59 m$^2$/gmSA) | — | 15.5 | 77.5 | 21,900 | 0.4 | — |
| 24 | 1% CuO(59 m$^2$/gmSA) | 2% I.CA-897 | 8.5 | 80.3 | 18,300 | 0.3 | — |
| 20 | 1% CuO(59 m$^2$/gmSA) + 0.33% Zn(Ac)$_2$.2H$_2$O | 2% M-2000 | 6.75 | 89.3 | 17,500 | 0.6 | — |
| 25 | 1% Cu dust + 0.33% Zn(Ac)$_2$.2H$_2$O | 2% I.CA-897 | 8.5 | 84.9 | 18,200 | 0.5 | — |
| 26 | 1% CuO(59 m$^2$/gmSA) + 0.08% Zn(Ac)$_2$.2H$_2$O | 2% I.CA-897 | 5 | 91.2 | 18,300 | 0.3 | — |

*Surfactants as previously described

TABLE III

Effect of Surfactant on Reaction
Experiments 20-23

| Exp. | Catalyst with or without surfactant | Hrs. Run | % True Yield p-NO$_2$DPA |
|---|---|---|---|
| 13 | 1.0% CuO, 59 m$^2$/gm no surfactant | 15¼ | 77.5 |
| 17 | 1.0% CuO + 0.33% Zn(Ac)$_2$.2H$_2$O | 8.75 | 84.4 |
| 20 | Ex. 17 + 2% by wt M-5000[a] | 6.75 | 89.3 |
| 21 | 1.0% CuO + 0.08% Zn(AC)$_2$.2H$_2$O | 9.5 | 85.8 |
| 22 | Ex. 21 + 2% by wt I. CA-897[b] | 5 | 91.2 |
| 18 | 1% Cu$_2$(CN)$_2$ | 14 | 80.5 |
| 19 | 1% Cu$_2$(CN)$_2$ + 0.33% Zn(Ac)$_2$.2H$_2$O | 6.5 | 92.9 |
| 23 | Ex. 19 2% I. CA-897 | 5 | 95.0 |

[a]Union Carbide's Carbowax Methoxy PEG-5000
[b]GAF's IGEPAL CA-897 Surfactant

From this data the preferred catalyst system from an environmental view as well as utilization of PCNB, speed of reaction and cost factors is that of Experiment 26.

It has been found that reducing the CuO:Zn(Ac)$_2$.2H$_2$O ratio from 1:1 to 1:0.33 to 1.0:0.16 to 1:0.08 (within experimental error) did not reduce the rate of reaction or lower the p-NO$_2$DPA content in the reaction. Only when the ratio was reduced to 1:0.04 did the reaction slow and yield of the product begin to fall.

It has been found that the minimum level of copper in the co-catalyst system necessary to get a good reaction appears to be approximately 1.0% by weight of PCNB.

To distinguish the present invention from Polish Pat. No. 101,496, the following experiments were performed in a manner similar to Experiment 1 except that the catalyst and amount of catalyst were varied. The reaction time was determined when less than 0.1 cc/hr of water was obtained from the reaction. The yield of p-NO$_2$DPA was determined by liquid chromatograph, using a silicon column. % DNTPA (dinitrotriphenylamine) was determined since DNTPA is an undesirable by-product. The % of PCNB remaining in the reaction mixture was also determined. % true yield of p-NO$_2$DPA is % crude yield times % p-NO$_2$DPA/100.

TABLE V

Experiments 37-48

| Exp. | % Catalyst | Hours Reaction Time | % True Yield p-NO$_2$DPA | % DNTPA | % PCNB |
|---|---|---|---|---|---|
| 27 | 1.0% Cu$_2$(CN)$_2$ | 14 | 86.4% | 4.9 | 0.3 |
| 28 | 1.0% Cu$_2$(CN)$_2$ + 0.08% Zn° dust | 14 | 85.4 | 4.6 | 0.2 |
| 29 | 1.0% Cu$_2$(CN)$_2$ + 0.40% ZN° dust | 13.5 | 88.0 | 5.3 | 1.0 |
| 30 | 1.0% Cu$_2$(CN)$_2$ + 2.0% ZN° dust | 13 | 90.1 | 4.6 | 1.1 |
| 31 | 1.0% Cu$_2$(CN)$_2$ + 0.33% Zn(Ac)$_2$.2H$_2$O | 6.5 | 88.7 | 5.4 | 1.3 |
| 32 | 1.0 Cu° (dust) | 26.75 | 80.6 | 8.6 | 0.1 |
| 33 | 1.0% Cu° dust + 2.0% Zn° dust | 25.25 | 75.5 | 5.0 | — |
| 34 | 1.0% Cu° dust + 2.0% Zn(Ac)$_2$.2H$_2$O | 16 | 80.3 | 5.9 | — |
| 35 | 1.0% Cu$_2$Cl$_2$ | 16.5 | 82.2 | 5.0 | — |
| 36 | 1.0% Cu$_2$Cl$_2$ + 0.40% Zn° dust | 16.5 | 79.0 | 6.9 | — |
| 37 | 1.0% Cu$_2$Cl$_2$ + 2.0% Zn° dust | 16.5 | 78.9 | 5.1 | — |
| 38 | 1.0% Cu$_2$Cl$_2$ + 0.40% Zn(AC)$_2$.2H$_2$O | 10 | 85.6 | 6.4 | 0.1 |
| 39 | 1.0% CuO(59 m$^2$/gm) | 15.5 | 75.8 | 5.1 | 1.4 |
| 40 | 1.0% CuO(59 m$^2$/gm) + 0.08% Zn° dust | 16.5 | 72.9 | 4.9 | 1.1 |
| 41 | 1.0% CuO(59 m$^2$/gm) + 0.40% Zn° dust | 16 | 75.2 | 5.0 | 0.9 |
| 42 | 1.0% CuO(59 m$^2$/gm) + 2.0% Zn° dust | 15.5 | 76.6 | 5.2 | 0.9 |

TABLE V-continued

Experiments 37–48

| Exp. | % Catalyst | Hours Reaction Time | % True Yield p-NO$_2$DPA | % DNTPA | % PCNB |
|---|---|---|---|---|---|
| 43 | 1.0% CuO(59 m$^2$/gm) + 0.04% Zn(Ac)$_2$.2H$_2$O | 12 | 83.2 | 5.1 | 0.5 |
| 44 | 1.0% CuO(59 m$^2$/gm) + 0.08% Zn(Ac)$_2$.2H$_2$O | 9.5 | 85.8 | 5.1 | — |
| 45 | 1.0% CuO(59 m$^2$/gm) + 0.16% Zn(Ac)$_2$.2H$_2$O | 9.75 | 84.6 | 5.1 | 0.4 |
| 46 | 1.0% CuO(59 m$^2$/gm) + 0.33% Zn(Ac)$_2$.2H$_2$O | 8.75 | 84.4 | 4.2 | — |
| 47 | 1.0% CuO(59 m$^2$/gm) + 1.0% Zn(Ac)$_2$.2H$_2$O | 9.25 | 87.8 | 7.6 | 0.6 |
| 48 | 2.0% CuO(59 m$^2$/gm) + 0.16% Zn(Ac)$_2$.2H$_2$O | 9.75 | 85.2 | 4.4 | 0.6 |

% p-NO$_2$DPA determined by gas chromatography

The data from Table V (Exp. 33 and 40–42) clearly indicates that the process of Polish Pat. No. 101,496 is inferior to the present invention in both required reaction time and yield of p-NO$_2$DPA.

These experiments demonstrate that small amounts of Zn++ compounds (preferably zinc acetate, Zn(Ac)$_2$.2H$_2$O; at levels of 0.08% or more based on the charged weight of para-chloronitrobenzene) act as co-catalysts with various copper catalysts; such as CuO, Cu° dust, Cu$_2$(CN)$_2$ or Cu$_2$Cl$_2$ (at the 1.0 part level, based on the weight of PCNB) in the production of p-NO$_2$DPA.

The addition of 0.33% Zn(Ac)$_2$.2H$_2$O to the reaction containing 1.0% CuO (59 meter$^2$/gram surface area of catalyst) reduced the reaction time from 15 to 8.75 hours and increased the p-NO$_2$DPA yield from 76 to 84% (Exp. 42 and 46).

The addition of a like amount of Zn(AC)$_2$.2H$_2$O to a reaction containing 1.0% Cu$_2$(CN)$_2$, Cu$_2$Cl$_2$ or Cu° dust gave similar results, in most cases.

The Polish Pat. No. 101,496 used 0.4% Zn dust with 0.8% Cu° dust at 198°–218° C. and got a 12½ hour reaction with a 74.6% yield of p-NO$_2$DPA. Increasing the level of Zn° dust to 2.0% with a 4.0% level of Cu° dust at 195°–218° C. gave a 9⅛ hour reaction with a 67.6% p-NO$_2$DPA yield.

Adding 0.94% Zn° dust to a 2.35% level of CuO catalyst and using a 23.6% level DMF in the Polish patent at 184°–6° C.; gave a 8–9 hour reaction with a 79–81.8% reported yield of p-NO$_2$DPA.

The use of Zn° dust in the reaction with CuO, Cu° dust or Cu$_2$Cl$_2$ gave little or no benefits (See Exps. 32, 33, 35, 36, 37, 39, 40, 41, and 42 in Table V).

The use of Zn(Ac)$_2$.2H$_2$O in the reaction with CuO, Cu° dust or Cu$_2$Cl$_2$ either increased the rate of reaction or yield of p-NO$_2$DPA or both (see Exps. 32, 34, 35, 38, 39, 41–48).

The use of Zn° dust with Cu$_2$(CN)$_2$ increased the p-NO$_2$DPA yield in the reaction 2–4% at the 0.4–2.0 part level, but only very slightly reduced the reaction times from 14 to 13.5–13 hours as the level of Zn° was increased from 0.4 to 2.0 parts. (See Exps. 27, 28, 29 and 30 in Table V).

A 0.08% level of Zn° dust with 1.0 Cu$_2$(CN)$_2$ was not effective.

The use of Zn(Ac)$_2$.2H$_2$O with Cu$_2$(CN)$_2$ not only increased the yield of p-NO$_2$DPA in the reaction, but reduced the reaction time by a factor of 2 (see Exps. 27 and 31).

While certain representative embodiments and details have been shown for the purposes of illustrating the invention, it will be apparent to those skilled in the art that various changes and modifications may be made herein without departing from the scope of the invention.

What is claimed:

1. A process wherein (1) a para-halonitrobenzene conforming to the following structural formula:

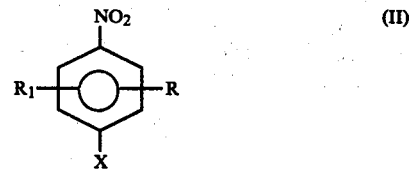

(II)

wherein R and R$_1$ are selected from the group consisting of hydrogen and alkyl radicals of 1 to 9 carbon atoms and wherein X is a halogen selected from the group consisting of chlorine and bromine is reacted with (2) a primary aromatic amine of the following structural formula:

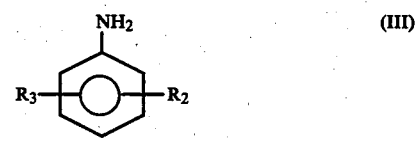

(III)

wherein R$_2$ and R$_3$ are radicals selected from the group consisting of hydrogen, alkyl radicals of 1 to 9 carbon atoms, alkoxy radicals of 1 to 9 carbon atoms and cycloalkyl radicals of 5 to 6 carbon atoms; (3) in the presence of a neutralizing agent selected from the group consisting of alkaline metal salts, oxides of alkali metal salts and alkali metal hydroxides; (4) a copper catalyst system at a concentration of at least 0.1 parts by weight per 100 parts by weight of the para-halonitrobenzene; (5) at a temperature of 100° to 250° C. (6) at a pressure from atmospheric to about 300 kPa and (7) with an excess of primary aromatic amine wherein the improvement is characterized in that the copper catalyst system has added thereto at least one zinc (II) compound selected from a group consisting of zinc (II) salts, zinc (II) oxides, zinc (II) sulfides and organometallic zinc (II) compounds.

2. The process according to claim 1 wherein the nitrogen containing aromatic compound is aniline.

3. The process of claim 1 wherein at least one zinc (II) compound is selected from the group consisting of zinc acetate, zinc sulfide, zinc stearate, zinc chloride, zinc oxide, zinc carbonate and zinc dimethyldithiocarbamate and is at least 5 percent by weight of the catalyst system.

4. The improved process recited in claim 2 wherein a solubilizing agent is incorporated into the reaction mixture at a concentration of (1) 0.25 to 4 parts when the nitrogen containing aromatic compound is aniline.

5. The process according to claim 1 wherein the copper compound is selected from the group comprising cupric oxide, cupric nitrate, copper acetyl-acetate, cupric chloride, cuprous chloride and powdered copper.

6. A process wherein (1) a para-halonitrobenzene conforming to the following structural formula:

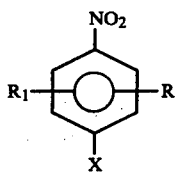
(II)

wherein R and $R_1$ are selected from the group consisting of hydrogen and alkyl radicals of 1 to 9 carbon atoms and wherein X is a halogen selected from the group consisting of chlorine and bromine is reacted; with (2) a primary aromatic amine of the following structural formula:

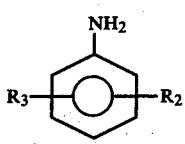
(III)

wherein $R_2$ and $R_3$ are radicals selected from the group consisting of hydrogen, alkyl radicals of 1 to 9 carbon atoms, alkoxy radicals of 1 to 9 carbon atoms and cycloalkyl radicals of 5 to 6 carbon atoms; (3) in the presence of a neutralizing agent selected from the group consisting of alkaline metal salts, oxides of alkali metal salts and alkali metal hydroxides; (4) a copper catalyst system at a concentration of at least 0.1 parts by weight per 100 parts by weight of the para-halonitrobenzene; (5) at a temperature of 100° to 250° C. (6) at a pressure from atmospheric to about 300 kPa, (7) with an excess of primary aromatic amine, and (8) a solubilizing agent, wherein the improvement is characterized in that the copper catalyst system has added thereto at least one zinc (II) compound selected from a group consisting of zinc (II) salts, zinc (II) oxides, zinc (II) sulfides and organometallic zinc (II) compounds.

7. The process according to claim 6 wherein the nitrogen containing aromatic compound is aniline.

8. The process of claim 8 wherein at least one zinc (II) is compound is selected from the group consisting of zinc acetate, zinc sulfide, zinc stearate, zinc oxide and zinc chloride.

9. The improved process recited in claim 6 wherein a solubilizing agent is incorporated into the reaction mixture at a concentration of (1) 0.25 to 4 parts when the nitrogen containing aromatic compound is aniline.

10. The process according to claim 6 wherein the copper compound is selected from the group comprising cupric oxide, cupric nitrate, copper acetyl-acetate, cupric chloride, cuprous chloride and powdered copper.

11. A process for producing p-nitrodiphenylamine from aniline and p-chloronitrobenzene wherein the reaction is conducted (a) at a temperature from 100° to 250° C., (b) in the presence of an alkaline metal salt, (c) with an excess of aniline, (d) at super atmospheric pressure, (e) in the presence of a solubilizing agent, (f) with at least 0.1 parts by weight per 100 parts by weight of the p-chloronitrobenzene of a catalyst, the improvement characterized in that the catalyst is a mixture of (A) at least one copper compound selected from a group comprising cupric oxide, cupric nitrate, cuprous cyanide, copper acetyl acetate, cupric chloride, cuprous chloride and powdered copper; and (B) at least one zinc (II) compound selected from a group comprising zinc acetate, zinc sulfide, zinc stearate, zinc oxide, zinc chloride, zinc carbonate and zinc dimethyldithiocarbamate.

12. A process according to claim 11 wherein the catalyst system consists of 1 part CuO and 0.08 parts of zinc acetate based on 100 parts of the p-chloronitrobenzene.

13. A process according to claim 11 wherein the catalyst system is from 1 to 3 parts by weight based on 100 parts of the p-chloronitrobenzene.

14. A process according to claim 11 wherein the catalyst system ratio of copper compounds to zinc (II) compounds ranges from 3:1 to 1:3.

15. A process according to claim 11 wherein the catalyst system is 50 percent copper oxide and 50 percent zinc acetate.

* * * * *